United States Patent
Holm et al.

(10) Patent No.: US 8,080,398 B2
(45) Date of Patent: *Dec. 20, 2011

(54) POLYPEPTIDES HAVING ALPHA-GLUCURONIDASE ACTIVITY AND POLYNUCLEOTIDES ENCODING SAME

(75) Inventors: Eva Hansen Holm, Vaerloese (DK); Dominique Aubert Skovland, Copenhagen (DK); Hanne Risbjerg Soerensen, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/959,669

(22) Filed: Dec. 3, 2010

(65) Prior Publication Data

US 2011/0091950 A1    Apr. 21, 2011

Related U.S. Application Data

(63) Continuation of application No. 12/742,971, filed as application No. PCT/EP2008/066241 on Nov. 26, 2008, now Pat. No. 7,867,745.

(60) Provisional application No. 60/991,026, filed on Nov. 29, 2007.

(30) Foreign Application Priority Data

Nov. 27, 2007 (EP) .................................. 07121642

(51) Int. Cl.
*C12N 9/24* (2006.01)
*C12P 7/06* (2006.01)
*C12P 1/00* (2006.01)

(52) U.S. Cl. ........................................ 435/161; 435/267
(58) Field of Classification Search ........................ None
See application file for complete search history.

(56) References Cited

FOREIGN PATENT DOCUMENTS

WO    WO 97/43423    5/1997

OTHER PUBLICATIONS

Chavez et al., Journal of Biotechnology, vol. 123, pp. 413-433 (2006).
De Vries et al., Journal of Bacteriology, vol. 180, No. 2, pp. 243-249 (1998).
De Wet et al., Enzyme and Microbial Technology, vol. 38, pp. 649-656 (2006).
Heneghan et al., Enzyme and Microbial Technology, vol. 41, pp. 677-682 (2007).
Petruccioli et al., Bioscience Biotechnology Biochemistry, vol. 63, No. 5, pp. 805-812 (1999).
Polizelli et al., Applied Microbiology and Biotechnology, vol. 67, pp. 577-591 (2005).

*Primary Examiner* — Nashaat Nashed
(74) *Attorney, Agent, or Firm* — Elias Lambiris

(57) ABSTRACT

The present invention relates to isolated polypeptides having alpha-glucuronidase activity and isolated polynucleotides encoding the polypeptides. The invention also relates to nucleic acid constructs, vectors, and host cells comprising the polynucleotides as well as methods of producing and using the polypeptides.

7 Claims, No Drawings

POLYPEPTIDES HAVING ALPHA-GLUCURONIDASE ACTIVITY AND POLYNUCLEOTIDES ENCODING SAME

CROSS-REFERENCE TO RELATED APPLICATIONS

This application is a continuation of U.S. application Ser. No. 12/742,971 filed on Jun. 2, 2010, now U.S. Pat. No. 7,867,745, which is a 35 U.S.C. 371 national application of PCT/EP2008/066241 filed Nov. 26, 2008, which claims priority or the benefit under 35 U.S.C. 119 of European application no. 07121642.8 filed Nov. 27, 2007 and U.S. provisional application No. 60/991,026 filed Nov. 29, 2007, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to isolated polypeptides having alpha-glucuronidase activity and isolated polynucleotides encoding the polypeptides. The invention also relates to nucleic acid constructs, vectors, and host cells comprising the polynucleotides as well as methods of producing and using the polypeptides.

2. Background

Plant cell wall polysaccharides constitute 90% of the plant cell wall and can be divided into three groups: cellulose, hemicellulose, and pectin. Cellulose represents the major constituent of call wall polysaccharides. Hemicelluloses are the second most abundant constituent of plant cell walls. The major hemicellulose polymer is xylan. The structure of xylans found in cell walls of plants can differ significantly depending on their origin, but they always contain a beta-1, 4-linked D-xylose backbone. The beta-1,4-linked D-xylose backbone can be substituted by various side groups, such as L-arabinose, D-galactose, acetyl, feruloyl, p-coumaroyl, and glucuronic acid residues.

Full hydrolysis of hemicellulose requires the action of a complex of enzymes including acetylxylan esterases, ferulic acid esterases, xylanases, arabinofuranosidases, xylosidases and alpha-glucuronidase. Alpha-glucuronidase is the enzyme that is responsible for hydrolysis of the alpha-1,2-glycosidic linkage between xylose and D-glucuronic acid or its 4-O-methyl ether.

It is an object of the present invention to provide novel polypeptides having alpha-glucuronidase activity suitable for use in industrial processes, e.g., in processes comprising conversion of cellulosic biomass into useful products including ethanol.

An alpha-glucuronidase from *Aureobasidium pullulans* being 67.3% identical has been disclosed by de Wet et al. (Enzyme Microb. Technol. 38:649-656, 2006).

SUMMARY OF THE INVENTION

The present invention relates to alpha-glucuronidases, and in particular to alpha-glucuronidases having an amino acid sequence homologous with or identical to the alpha-glucuronidase derived from *Penicillium aurantiogriseum* and disclosed in SEQ ID NO:2.

In a first aspect the present invention provides an isolated polypeptide having alpha-glucuronidase activity, selected from the group consisting of:

(a) a polypeptide comprising an amino acid sequence having at least 75%, more preferably at least 80%, more preferably at least 85%, even more preferably at least 85%, most preferably at least 90%, and even most preferably at least 95% identity to the mature polypeptide of SEQ ID NO:2;

(b) a polypeptide encoded by a polynucleotide that hybridizes under at least high stringency conditions with (i) the mature polypeptide coding sequence of SEQ ID NO:1, (ii) genomic DNA sequence comprising the mature polypeptide coding sequence of SEQ ID NO:1, or (iii) a full-length complementary strand of (i) or (ii);

(c) a polypeptide encoded by a polynucleotide comprising a nucleotide sequence having at least 75%, more preferably at least 80%, more preferably at least 85%, even more preferably at least 85%, most preferably at least 90%, and even most preferably at least 95% identity to the mature polypeptide coding sequence of SEQ ID NO:1;

(d) a variant comprising a substitution, deletion, and/or insertion of one or more (several) amino acids of the mature polypeptide of SEQ ID NO:2.

In a second aspect the present invention provides an isolated polynucleotide comprising a nucleotide sequence that encodes the polypeptide of the first aspect.

In a third aspect the present invention provides a nucleic acid construct comprising the polynucleotide of the second aspect operably linked to one or more (several) control sequences that direct the production of the polypeptide in an expression host.

In a fourth aspect the present invention provides a recombinant expression vector comprising the nucleic acid construct of the third aspect.

In a fifth aspect the present invention provides a recombinant host cell comprising the nucleic acid construct of the third aspect.

In a sixth aspect the present invention provides a method of producing the polypeptide of the first aspect, comprising: (a) cultivating a cell, which in its wild-type form produces the polypeptide, under conditions conducive for production of the polypeptide; and (b) recovering the polypeptide.

In a seventh aspect the present invention provides a method of producing the polypeptide of the first aspect, comprising: (a) cultivating a host cell comprising a nucleic acid construct comprising a nucleotide sequence encoding the polypeptide under conditions conducive for production of the polypeptide; and (b) recovering the polypeptide.

In an eighth aspect the present invention provides a method of producing the polypeptide of the first aspect, comprising: (a) cultivating a transgenic plant or a plant cell comprising a polynucleotide encoding the polypeptide under conditions conducive for production of the polypeptide; and (b) recovering the polypeptide.

In a ninth aspect the present invention provides a method of transgenic plant, plant part or plant cell transformed with a polynucleotide encoding the polypeptide of the first aspect.

In a tenth aspect the present invention provides a method of producing a protein, comprising: (a) cultivating the recombinant host cell of the fifth aspect under conditions conducive for production of the protein; and (b) recovering the protein.

In an 11th aspect the present invention provides a method for degrading or converting a biomass material, comprising treating the material with the polypeptide of the first aspect.

In a 12th aspect the present invention provides a composition comprising the polypeptide of the first aspect, and one or more enzyme(s) selected from acetylxylan esterase, ferulic acid esterase, xylanase, arabinofuranosidase and xylosidase.

In a 13th aspect the present invention provides a use of the polypeptide of the first aspect or the composition of the 12th aspect in a process for hydrolysis of a biomass material comprising contacting said biomass with said polypeptide or said composition.

DEFINITIONS

Alpha-glucuronidase activity: The term "alpha-glucuronidase activity" is defined herein as an EC 3.2.1.139 activity that catalyzes the reaction alpha-D-glucuronoside+ H2O=an alcohol+D-glucuronate. For purposes of the present invention, alpha-glucuronidase activity is determined according to the procedure described by de Vries (J. Bacteriol, 1998, Vol. 180, p. 243-249). One unit of alpha-glucuronidase activity equals the amount of enzyme capable 1 micromole of glucuronic or 4-O-methylglucuronic acid per min under the standard assay conditions described in the section titled "Determining alpha-glucuronidase activity".

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the alpha-glucuronidase activity of the mature polypeptide of SEQ ID NO:2.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having alpha-glucuronidase activity that is in its final form following translation and any post-translational modifications, such as N-terminal processing, C-terminal truncation, glycosylation, phosphorylation, etc. In a preferred aspect, the mature polypeptide is amino acids 1 to 835 of SEQ ID NO:2.

Mature polypeptide coding sequence: The term "mature polypeptide coding sequence" is defined herein as a nucleotide sequence that encodes a mature polypeptide having alpha-glucuronidase activity. In a preferred aspect, the mature polypeptide coding sequence is nucleotides 1 to 2508 of SEQ ID NO:1.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the mature polypeptide of SEQ ID NO:2.

Alternatively, the term "homologous sequence" is defined as an amino acid sequence having a degree of identity to the mature polypeptide of SEQ ID NO:2 of preferably at least 75%, more preferably at least 80%, more preferably at least 85%, even more preferably at least 90%, most preferably at least 95%, and even most preferably at least 96%, at least 97%, at least 98%, or at least 99%, which has alpha-glucuronidase activity Polypeptide fragment: The term "polypeptide fragment" is defined herein as a polypeptide having one or more (several) amino acids deleted from the amino and/or carboxyl terminus of the mature polypeptide of SEQ ID NO:2; or a homologous sequence thereof; wherein the fragment has alpha-glucuronidase activity. In a preferred aspect, a fragment contains at least 500 amino acid residues, more preferably at least 600 amino acid residues, and most preferably at least 700 amino acid residues, such as at least 800 amino acid residues of the mature polypeptide of SEQ ID NO:2 or a homologous sequence thereof.

Subsequence: The term "subsequence" is defined herein as a nucleotide sequence having one or more (several) nucleotides deleted from the 5' and/or 3' end of the mature polypeptide coding sequence of SEQ ID NO:1; or a homologous sequence thereof; wherein the subsequence encodes a polypeptide fragment having alpha-glucuronidase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO:2; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having alpha-glucuronidase activity produced by an organism expressing a modified polynucleotide sequence of the mature polypeptide coding sequence of SEQ ID NO:1; or a homologous sequence thereof. The modified nucleotide sequence is obtained through human intervention by modification of the polynucleotide sequence disclosed in SEQ ID NO:1; or a homologous sequence thereof.

Glycoside Hydrolase (GH) families: The numbering of GH families applied in this disclosure follows the concept of Coutinho, P. M. & Henrissat, B. (1999) CAZ—Carbohydrate Active Enzymes server at URL: afmb.cnrs-mrs.fr/~cazy/CAZY/index.html or alternatively Coutinho, P. M. & Henrissat, B. 1999; The modular structure of cellulases and other carbohydrate-active enzymes: an integrated database approach. In "*Genetics, Biochemistry and Ecology of Cellulose Degradation*", K. Ohmiya, K. Hayashi, K. Sakka, Y. Kobayashi, S. Karita and T. Kimura eds., Uni Publishers Co., Tokyo, pp. 15-23, and in Bourne, Y. & Henrissat, B. 2001; Glycoside hydrolases and glycosyltransferases: families and functional modules, *Current Opinion in Structural Biology* 11:593-600. A polypeptide of the present invention is preferably of the GH family 67.

DETAILED DESCRIPTION OF THE INVENTION

Polypeptides Having Alpha-Glucuronidase Activity

In a preferred aspect, the present invention relates to isolated polypeptides comprising an amino acid sequence having a degree of identity to the mature polypeptide of SEQ ID NO:2 of preferably at least 75%, more preferably at least 80%, more preferably at least 85%, even more preferably at least 90%, most preferably at least 95%, and even most preferably at least 96%, at least 97%, at least 98%, or at least 99%, which have alpha-glucuronidase activity (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO:2.

A polypeptide of the present invention preferably comprises the amino acid sequence of SEQ ID NO:2 or an allelic variant thereof; or a fragment thereof having alpha-glucuronidase activity. In a preferred aspect, the polypeptide comprises the amino acid sequence of SEQ ID NO:2. In another preferred aspect, the polypeptide comprises the mature polypeptide of SEQ ID NO:2. In another preferred aspect, the polypeptide comprises amino acids 1 to 835 of SEQ ID NO:2, or an allelic variant thereof; or a fragment thereof having alpha-glucuronidase activity. In another preferred aspect, the polypeptide comprises amino acids 1 to 835 of SEQ ID NO:2. In another preferred aspect, the polypeptide consists of the amino acid sequence of SEQ ID NO:2 or an allelic variant thereof; or a fragment thereof having alpha-glucuronidase activity. In another preferred aspect, the polypeptide consists of the amino acid sequence of SEQ ID NO:2. In another preferred aspect, the polypeptide consists of the mature polypeptide of SEQ ID NO:2. In another preferred aspect, the polypeptide consists of amino acids 1 to 835 of SEQ ID NO:2 or an allelic variant thereof; or a fragment thereof having alpha-glucuronidase activity. In another preferred aspect, the polypeptide consists of amino acids 1 to 835 of SEQ ID NO:2.

In preferred aspect, the present invention relates to isolated polypeptides having alpha-glucuronidase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO:1, (ii) the genomic DNA sequence comprising the mature polypeptide coding sequence of SEQ ID NO:1, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual*, 2d edition, Cold Spring Harbor, New York). A subsequence of the mature polypeptide coding sequence of SEQ ID NO:1 contains at least 100 contiguous nucleotides or preferably at least 200 contiguous nucleotides. Moreover, the subsequence may encode a polypeptide fragment having alpha-glucuronidase activity. In a preferred aspect, the complementary strand is the full-length complementary strand of the mature polypeptide coding sequence of SEQ ID NO:1.

The nucleotide sequence of SEQ ID NO:1; or a subsequence thereof; as well as the amino acid sequence of SEQ ID NO:2; or a fragment thereof; may be used to design nucleic acid probes to identify and clone DNA encoding polypeptides having alpha-glucuronidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having alpha-glucuronidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO:1; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO:1; the genomic DNA sequence comprising the mature polypeptide coding sequence of SEQ ID NO:1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO:1. In another preferred aspect, the nucleic acid probe is nucleotides 1 to 2508 of SEQ ID NO:1. In another preferred aspect, the nucleic acid probe is a polynucleotide sequence that encodes the polypeptide of SEQ ID NO:2, or a subsequence thereof. In another preferred aspect, the nucleic acid probe is SEQ ID NO:1.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In another aspect, the present invention relates to isolated polypeptides having alpha-glucuronidase activity encoded by polynucleotides comprising or consisting of nucleotide sequences that have a degree of identity to the mature polypeptide coding sequence of SEQ ID NO:1 of preferably at least 75%, more preferably at least 80%, more preferably at least 85%, even more preferably at least 90%, most preferably at least 95%, and even most preferably 96%, 97%, 98%, or 99%, which encode an active polypeptide. See polynucleotide section herein.

In another aspect, the present invention relates to artificial variants comprising a substitution, deletion, and/or insertion of one or more (or several) amino acids of the mature polypeptide of SEQ ID NO:2; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081 to 1085). In the latter technique, single alanine mutations are introduced at every residue in the molecule, and the resultant mutant molecules are tested for biological activity (i.e., alpha-glucuronidase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO:2, such as amino acids 1 to 835 of SEQ ID NO:2, is 10, preferably 9, more preferably 8, more preferably 7, more preferably at most 6, more preferably 5, more preferably 4, even more preferably 3, most preferably 2, and even most preferably 1.
Sources of Polypeptides Having Alpha-Glucuronidase Activity A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having alpha-glucuronidase activity of the present invention is preferably a fungal polypeptide, and more preferably a yeast polypeptide such as a *Candida, Kluyveromyces, Pichia, Saccharomyces, Schizosaccharomyces,* or *Yarrowia* polypeptide having alpha-glucuronidase activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having alpha-glucuronidase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having alpha-glucuronidase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* polypeptide having alpha-glucuronidase activity.

In another preferred aspect, the polypeptide is a *Penicillium* polypeptide, and preferably a *Penicillium aurantiogriseum* polypeptide.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to isolated polynucleotides comprising or consisting of nucleotide sequences that encode polypeptides having alpha-glucuronidase activity of the present invention.

In a preferred aspect, the nucleotide sequence comprises or consists of SEQ ID NO:1. In another preferred aspect, the nucleotide sequence comprises or consists of the mature polypeptide coding sequence of SEQ ID NO:1. In another preferred aspect, the nucleotide sequence comprises or consists of nucleotides 1 to 2508 of SEQ ID NO:1. The present invention also encompasses nucleotide sequences that encode polypeptides comprising or consisting of the amino acid sequence of SEQ ID NO:2 or the mature polypeptide thereof, which differ from SEQ ID NO:1 or the mature polypeptide coding sequence thereof by virtue of the degeneracy of the genetic code. The present invention also relates to subsequences of SEQ ID NO:1 that encode fragments of SEQ ID NO:2 that have alpha-glucuronidase activity.

The present invention also relates to mutant polynucleotides comprising or consisting of at least one mutation in the mature polypeptide coding sequence of SEQ ID NO:1, in which the mutant nucleotide sequence encodes the mature polypeptide of SEQ ID NO:2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Penicillium*, preferably *Penicillium aurantiogriseum*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO:1 of at least 75%, more preferably at least 80%, more preferably at least 85%, even more preferably at least 90%, most preferably at least 95%, and even most preferably at least 96%, at least 97%, at least 98%, or at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO:1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for alpha-glucuronidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO:1, (ii) the genomic DNA sequence comprising the mature polypeptide coding sequence of SEQ ID NO:1, or (iii) a full-length complementary strand of (i) or (ii); or allelic variants and subsequences thereof (Sambrook et al., 1989, supra), as defined herein. In a preferred aspect, the complementary strand is the full-length complementary strand of the mature polypeptide coding sequence of SEQ ID NO:1.

The present invention also relates to isolated polynucleotides obtained by (a) hybridizing a population of DNA under very low, low, medium, medium-high, high, or very high stringency conditions with (i) the mature polypeptide coding sequence of SEQ ID NO:1, (ii) the genomic DNA sequence comprising the mature polypeptide coding sequence of SEQ ID NO:1, or (iii) a full-length complementary strand of (i) or (ii); and (b) isolating the hybridizing polynucleotide, which encodes a polypeptide having alpha-glucuronidase activity. In a preferred aspect, the complementary strand is the full-length complementary strand of the mature polypeptide coding sequence of SEQ ID NO:1.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and Aspergillus nidulans triose phosphate isomerase.

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

Examples of origins of replication useful in a filamentous fungal cell are AMA1 and ANS1 (Gems et al., 1991, Gene 98: 61 to 67; Cullen et al., 1987, Nucleic Acids Research 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a Candida, Hansenula, Kluyveromyces, Pichia, Saccharomyces, Schizosaccharomyces, or Yarrowia cell.

In a most preferred aspect, the yeast host cell is a Saccharomyces carlsbergensis, Saccharomyces cerevisiae, Saccharomyces diastaticus, Saccharomyces douglasii, Saccharomyces kluyveri, Saccharomyces norbensis, or Saccharomyces oviformis cell. In another most preferred aspect, the yeast host cell is a Kluyveromyces lactis cell. In another most preferred aspect, the yeast host cell is a Yarrowia lipolytica cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

In an even more preferred aspect, the filamentous fungal host cell is an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

In a most preferred aspect, the filamentous fungal host cell is an Aspergillus awamori, Aspergillus fumigatus, Aspergillus foetidus, Aspergillus japonicus, Aspergillus nidulans, Aspergillus niger or Aspergillus oryzae cell. In another most preferred aspect, the filamentous fungal host cell is a Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, or Fusarium venenatum cell. In another most preferred aspect, the filamentous fungal host cell is a Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus and Tricho-

*derma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, 194: 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Penicillium*. In a more preferred aspect, the cell is *Penicillium aurantiogriseum*.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO:1, wherein the mutant nucleotide sequence encodes a polypeptide that comprises or consists of the mature polypeptide of SEQ ID NO:2, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having alpha-glucuronidase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mol. Biol.* 18: 675-689; Zhang et al., 1991, *Plant Cell* 3: 1155-1165). organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991 to 1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having alpha-glucuronidase activity of the present invention under conditions conducive for production of the polypeptide; and (b) recovering the polypeptide.

Compositions

The present invention also relates to compositions comprising a polypeptide of the present invention.

The composition may comprise a polypeptide of the present invention as the major enzymatic component, e.g., a mono-component composition. Alternatively, the composition may comprise multiple enzymatic activities, such as an acetylxylan esterase, arabinofuranosidase, aminopeptidase, amylase, carbohydrase, carboxypeptidase, catalase, cellulase, chitinase, cutinase, cyclodextrin glycosyltransferase, deoxyribonuclease, esterase, ferulic acid esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, xylanase or xylosidase.

The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having alpha-glucuronidase activity, or compositions thereof.

A polypeptide having alpha-glucuronidase activity of the present invention may be used in several applications to degrade or convert a biomass material, i.e., a material comprising glucuronic acid-substituted xylan by treating the material with an effective amount of the polypeptide.

The polypeptides of the present invention are preferably used in conjunction with other xylan degrading enzymes such as acetylxylan esterases, ferulic acid esterases, xylanases, arabinofuranosidases, and xylosidases in processes wherein xylan has to be degraded.

The polypeptides having alpha-glucuronidase activity are useful in a number of applications: modification of glucuronic acid-substituted xylan containing animal feeds to improve digestability; general applications resulting from biomass degradation or conversion to fermentable sugars in the production of, for example, fuel and/or potable ethanol; processing aids used in pulp and paper de-lignification; component of enzymatic scouring systems for textiles; food applications, e.g., baking, in combination with other enzymatic functionalities to improve the physical properties of baked goods; and laundry detergent applications in combination with other enzyme functionalities. The polypeptides or composition may be used. for producing or modifying a nutritional/dietary fibre and/or for producing a xylose, arabinose and/or linear xylose or for producing derivatives of xylose, arabinose by fermentation, enzymatic processing or chemical synthesis.

Preferably the biomass material, i.e., a material comprising glucuronic acid-substituted xylan is selected from the list consisting of herbaceous and/or woody energy crops, agricultural food and feed crops, animal feed products, tubers, roots, stems, legumes, cassava peels, cocoa pods, rice husks and/or hulls, rice bran, cobs, straw, hulls, husks, sugar beet pulp, locust bean pulp, vegetable pomaces, agricultural crop waste, straw, stalks, leaves, corn bran, husks, cobs, rind, shells, pods, wood waste, bark, shavings, sawdust, wood pulp, pulping liquor, waste paper, cardboard, wood waste, industrial or municipal waste water solids, manure, by-product from brewing and/or fermentation processes, wet distillers grain, dried distillers grain, spent grain, vinasse and bagasse.

In an embodiment the polypeptide having alpha-glucuronidase activity is used in a process comprising hydrolysis of a cellulosic biomass, said process comprising contacting the biomass with the polypeptide, e.g., in a process for producing ethanol from cellulosic biomass or for improving the nutritional value of animal feed. In a preferred embodiment the polypeptide having alpha-glucuronidase activity is used for degrading the cellulosic part of a substrate primarily consisting of starch, e.g., the milled grain slurry in a process comprising producing a starch hydrolysis, e.g., such as in a starch based fermentation process, e.g., an ethanol process.

Determining Alpha-Glucuronidase Activity

For purposes of the present invention, alpha-glucuronidase activity is determined according to the procedure described by de Vries (*J. Bacteriol.* 180: 243-249 (1998)). One alpha-glucuronidase unit is the amount of enzyme liberating 1 micromol of glucuronic or 4-O-methylglucuronic acid per min under the standard assay conditions below.

The incubation mixture for the alpha-glucuronidase assay (total volume, 0.2 ml) contains 0.16 ml of substrate (2 mg of aldotriouronic acid-aldobiuronic acid [80:20] in 0.05 M sodium acetate buffer [pH 5.0]) and 0.04 ml of enzyme solution to be assayed. The incubation is started by addition of the enzyme. After 30 min of incubation at 40° C., the reaction is stopped by boiling the samples for 4 min. Precipitates are removed by centrifugation (10,000×g), after which the supernatant is transferred to a new tube. To each tube, 0.6 ml of copper reagent prepared as described by Milner and Avigad (*Carbohydr. Res.* 4: 359-361 (1967)) is added, and then the sample is boiled for 10 min and cooled on ice. Subsequently, 0.4 ml of arsenomolybdate reagent prepared as described by Nelson (Biol. Chem. 1944, 153:375-380) is added. The samples are mixed gently, 0.8 ml of $H_2O$ is added, and the absorbance at 600 nm is measured against $H_2O$. Controls are prepared by boiling a complete assay mixture at time zero, before incubation at 40° C. A substrate control is made by adding water instead of enzyme solution. A standard curve is prepared by using D-glucuronic acid.

Specificity of the Alpha-Glucuronidase

The specificity of the alpha-glucuronidases from *P. aurantiogriseum* was investigated by means of $^1H$ NMR. The enzyme (0.7 µg EP/mg substrate) were incubated with oligomers (10 mg/mL) at pH 5.5 (50 mM NaOAc) overnight at 30° C. before inactivated at 95° C. for 20 min. The samples were freeze-dried and dissolved in $D_2O$ (1 mL). $^1H$ NMR spectra were recorded on a Varian Mercury 400 MHz at 30° C. and 80° C., respectively. Data were collected over 100 scans and the HDO signal was used as a reference signal (4.67 ppm). Spectra are not attached.

The alpha-glucuronidase was found to be active on 4-OMe-alpha-glucuronopyranosyl substituted xylo-oligomers generated by a GH10 xylanase. It did not show any activity on oligomers formed by a GH11 xylanase or on xylan polymeric substances. This indicates that the alpha-glucuronidase has activity on 4-OMe-GlcA's terminal xylose units only and no activity on "internal" glucuronoside residues.

---

The invention claimed is:

1. An isolated polypeptide having alpha-glucuronidase activity, which has at least 90% sequence identity to the polypeptide of SEQ ID NO:2.

2. A composition comprising the polypeptide of claim 1 and one or more enzymes selected from the group consisting of acetylxylan esterase, arabinofuranosidase, ferulic acid esterase xylanase, and xylosidase.

3. A method for degrading or converting a biomass material, comprising treating the biomass material with the polypeptide of claim 1.

4. The method of claim 3, further comprising treating the biomass material comprising feruloyl groups with one or more enzymes selected from the group consisting of arabinofuranosidase, xylanase, and xylosidase.

5. The method of claim 3, wherein the biomass material is an animal feed.

6. The method of claim 3, wherein the biomass material is a cellulosic biomass.

7. The method of claim 3, which is a process for producing ethanol.

* * * * *

SEQUENCE LISTING

<160> NUMBER OF SEQ ID NOS: 2

<210> SEQ ID NO 1
<211> LENGTH: 2508
<212> TYPE: DNA
<213> ORGANISM: Penicillium aurantiogriseum
<220> FEATURE:
<221> NAME/KEY: CDS
<222> LOCATION: (1)..(2508)

<400> SEQUENCE: 1 atg cgt gca ctt ctc ttc ttc gcc tcc ttg ggc ttt gca gcc gct gag    48

```
Met Arg Ala Leu Leu Phe Phe Ala Ser Leu Gly Phe Ala Ala Ala Glu
1               5                   10                  15 aac ggc ctc aat ggc tgg ctg cgg tac gca tca tta ccc tgt tca ggc         96
Asn Gly Leu Asn Gly Trp Leu Arg Tyr Ala Ser Leu Pro Cys Ser Gly
            20                  25                  30 caa tgt cat ccc aac ctc cct tcg agt atc gtc acc ctc aat gcg act        144
Gln Cys His Pro Asn Leu Pro Ser Ser Ile Val Thr Leu Asn Ala Thr
        35                  40                  45 gag aca agt ccg gta tat gtt gcg ggg acg gag ttg caa agt ggt ctc        192
Glu Thr Ser Pro Val Tyr Val Ala Gly Thr Glu Leu Gln Ser Gly Leu
    50                  55                  60 aaa ggc gtt tat ggg aag agt gtc caa gtc gca cac aac aag tgc aag        240
Lys Gly Val Tyr Gly Lys Ser Val Gln Val Ala His Asn Lys Cys Lys
65              70                  75                  80 aca tcc tcc tcg gtt gtt gtt ggc acg gtt gat caa tat cgg gaa agc        288
Thr Ser Ser Ser Val Val Val Gly Thr Val Asp Gln Tyr Arg Glu Ser
                85                  90                  95 tgt ggc cct gtg aaa aac gta ccc gaa ctg gaa gaa gat ggc ttc tgg        336
Cys Gly Pro Val Lys Asn Val Pro Glu Leu Glu Glu Asp Gly Phe Trp
            100                 105                 110 ctc gat acc aag ggg gaa aac gtt caa atc ctt ggg caa aac gag agg        384
Leu Asp Thr Lys Gly Glu Asn Val Gln Ile Leu Gly Gln Asn Glu Arg
        115                 120                 125 ggt gct ctc tat ggc acc ttt gaa tac ttg tcg atg ctc gca cag gga        432
Gly Ala Leu Tyr Gly Thr Phe Glu Tyr Leu Ser Met Leu Ala Gln Gly
    130                 135                 140 aac ttc tcc aag gtc gca tat gcg tcc aat cct tct gcc cca att cgc        480
Asn Phe Ser Lys Val Ala Tyr Ala Ser Asn Pro Ser Ala Pro Ile Arg
145                 150                 155                 160 tgg gtg aat caa tgg gat gac ctg gat gga aga atc gaa cgc ggc tat        528
Trp Val Asn Gln Trp Asp Asp Leu Asp Gly Arg Ile Glu Arg Gly Tyr
            165                 170                 175 ggt ggc ccc tct atc ttc ttc aag gac ggt caa atc gtc gac gac cta        576
Gly Gly Pro Ser Ile Phe Phe Lys Asp Gly Gln Ile Val Asp Asp Leu
        180                 185                 190 aca cgg gtt act gaa tac gcc cgt ttg ttg gcc tcg atc aga atc aat        624
Thr Arg Val Thr Glu Tyr Ala Arg Leu Leu Ala Ser Ile Arg Ile Asn
    195                 200                 205 gct gtc gtc att aac aat gtc aat gcg gat gct gct ctc ttg aat tcc        672
Ala Val Val Ile Asn Asn Val Asn Ala Asp Ala Ala Leu Leu Asn Ser
210                 215                 220 aca aac ctc gac ggc gtg gct cga atc gct gat gtc ttc cgc cca tac        720
Thr Asn Leu Asp Gly Val Ala Arg Ile Ala Asp Val Phe Arg Pro Tyr
225                 230                 235                 240 ggt ata caa gtc ggc cta tcg ctc aat ttc gca tcc cct aaa acg gat        768
Gly Ile Gln Val Gly Leu Ser Leu Asn Phe Ala Ser Pro Lys Thr Asp
            245                 250                 255 gga gga ctc aac act ttt gat ccc ctc gat gca tct gtc atc gag tgg        816
Gly Gly Leu Asn Thr Phe Asp Pro Leu Asp Ala Ser Val Ile Glu Trp
        260                 265                 270 tgg tcg aat att aca acc cag gtc tat gag cga gtt cct gac atg gct        864
Trp Ser Asn Ile Thr Thr Gln Val Tyr Glu Arg Val Pro Asp Met Ala
    275                 280                 285 ggc tat ctg gtc aag gct gac tcg gag gga gag cca ggc ccc cag aca        912
Gly Tyr Leu Val Lys Ala Asp Ser Glu Gly Glu Pro Gly Pro Gln Thr
290                 295                 300 tat aac aga acg ctc gca gaa gcg gcg aac ctt ttc gcc aaa gaa gtc        960
Tyr Asn Arg Thr Leu Ala Glu Ala Ala Asn Leu Phe Ala Lys Glu Val
305                 310                 315                 320 cag ccc tac ggt ggc att gtt atg tat cgc gcg ttt gtc tac aat aag       1008
```

```
Gln Pro Tyr Gly Gly Ile Val Met Tyr Arg Ala Phe Val Tyr Asn Lys
                325                 330                 335 cta aac gaa tca atc tgg acg gat gat cgt gca aag gct gcc gtg gga      1056
Leu Asn Glu Ser Ile Trp Thr Asp Asp Arg Ala Lys Ala Ala Val Gly
            340                 345                 350 ttt ttc aag gat cta gat ggc gaa ttt gac gac aat gtg gtg atc caa      1104
Phe Phe Lys Asp Leu Asp Gly Glu Phe Asp Asp Asn Val Val Ile Gln
        355                 360                 365 atc aag tac ggg cct att gat ttc cag gtc cgt gaa cca gca tcg gca      1152
Ile Lys Tyr Gly Pro Ile Asp Phe Gln Val Arg Glu Pro Ala Ser Ala
    370                 375                 380 ttg ttt gca aat ttg ttc aac acc agc atg gcc att gaa cta cag gtt      1200
Leu Phe Ala Asn Leu Phe Asn Thr Ser Met Ala Ile Glu Leu Gln Val
385                 390                 395                 400 acg caa gaa tat ctt gga caa cag tcg cat ttg gtc tat gtt gct cct      1248
Thr Gln Glu Tyr Leu Gly Gln Gln Ser His Leu Val Tyr Val Ala Pro
                405                 410                 415 ctt tgg aag acg atc tta gac tct gac ctc cgc gtc gac ggc cag cca      1296
Leu Trp Lys Thr Ile Leu Asp Ser Asp Leu Arg Val Asp Gly Gln Pro
            420                 425                 430 tca ctc gtt cgc gat att gtg act ggt aaa cgg ttc aat cgc aaa ctg      1344
Ser Leu Val Arg Asp Ile Val Thr Gly Lys Arg Phe Asn Arg Lys Leu
        435                 440                 445 ggt gga tca gca gct gtt gtc aac gtg ggc aca aac acc acc tgg ctt      1392
Gly Gly Ser Ala Ala Val Val Asn Val Gly Thr Asn Thr Thr Trp Leu
    450                 455                 460 ggt agc cac ctg tct atg tca aat cta tat gcc tac ggt cgc tta gct      1440
Gly Ser His Leu Ser Met Ser Asn Leu Tyr Ala Tyr Gly Arg Leu Ala
465                 470                 475                 480 tgg aac cca gca gat gat gcc caa gac att ctg caa gac tgg atc aga      1488
Trp Asn Pro Ala Asp Asp Ala Gln Asp Ile Leu Gln Asp Trp Ile Arg
                485                 490                 495 ctg acc ttt ggg ctc gac cgg aag gta ctt gac acc atc act cgc atg      1536
Leu Thr Phe Gly Leu Asp Arg Lys Val Leu Asp Thr Ile Thr Arg Met
            500                 505                 510 tcc atg gaa tct tgg ccc gcc tac gaa caa tac agt ggg aat ttg ggc      1584
Ser Met Glu Ser Trp Pro Ala Tyr Glu Gln Tyr Ser Gly Asn Leu Gly
        515                 520                 525 ata cag act tta aca gat att tta tac act cac tat ggt ccc aac cct      1632
Ile Gln Thr Leu Thr Asp Ile Leu Tyr Thr His Tyr Gly Pro Asn Pro
    530                 535                 540 gca tcc caa gac aac aat gga tgg ggc caa tgg acc cgc gca gac caa      1680
Ala Ser Gln Asp Asn Asn Gly Trp Gly Gln Trp Thr Arg Ala Asp Gln
545                 550                 555                 560 acc agt att gga atg gat cgg aca gtg gca aac ggc aca ggc ttt tcg      1728
Thr Ser Ile Gly Met Asp Arg Thr Val Ala Asn Gly Thr Gly Phe Ser
                565                 570                 575 ggc cag tat ccg gat gaa atc gct gcc atg tat gag aac atc gac acc      1776
Gly Gln Tyr Pro Asp Glu Ile Ala Ala Met Tyr Glu Asn Ile Asp Thr
            580                 585                 590 acg cca gac gat ctt cta cta tgg ttc cac cat gtg aaa tac acc cat      1824
Thr Pro Asp Asp Leu Leu Leu Trp Phe His His Val Lys Tyr Thr His
        595                 600                 605 cgt ctg cac tcg ggg aag acc gtt att caa cac ttc tac gat gaa cac      1872
Arg Leu His Ser Gly Lys Thr Val Ile Gln His Phe Tyr Asp Glu His
    610                 615                 620 tac agc ggg gcg gaa act gca cag aca ttc ttt acg caa tgg gaa tca      1920
Tyr Ser Gly Ala Glu Thr Ala Gln Thr Phe Leu Thr Gln Trp Glu Ser
625                 630                 635                 640 ctt cat ggc aaa att gat gct gag cga tac aat cat act cgg cac ttc      1968
Leu His Gly Lys Ile Asp Ala Glu Arg Tyr Asn His Thr Arg His Phe
```

```
                Leu His Gly Lys Ile Asp Ala Glu Arg Tyr Asn His Thr Arg His Phe
                                645                 650                 655 cta gac tac cag agc ggt cac tca att gtg tgg aga gat gcg att aat      2016
Leu Asp Tyr Gln Ser Gly His Ser Ile Val Trp Arg Asp Ala Ile Asn
                660                 665                 670 gac ttc tat tac aat ctt tcc ggg atc cct gat gag gcc aag cgt gtc      2064
Asp Phe Tyr Tyr Asn Leu Ser Gly Ile Pro Asp Glu Ala Lys Arg Val
            675                 680                 685 ggc cac cac cca tgg cgc atc gaa gcg gaa gat atg aag tta gag ggc      2112
Gly His His Pro Trp Arg Ile Glu Ala Glu Asp Met Lys Leu Glu Gly
        690                 695                 700 tac aaa act tac acc gtc agc ccc ttc gaa aca gct tct ggt tcg gtt      2160
Tyr Lys Thr Tyr Thr Val Ser Pro Phe Glu Thr Ala Ser Gly Ser Val
705                 710                 715                 720 gcc att gtt aca act tcc aac agt aca gcc ggc acc gct tca acc aaa      2208
Ala Ile Val Thr Thr Ser Asn Ser Thr Ala Gly Thr Ala Ser Thr Lys
                725                 730                 735 ata aac ttt ccc tct ggc acc tat gac ctt gca gtg aac tac tac gat      2256
Ile Asn Phe Pro Ser Gly Thr Tyr Asp Leu Ala Val Asn Tyr Tyr Asp
                740                 745                 750 gta tac ggt ggc cag tcg cag tgg agg gtc tat ctg aat aat cag gaa      2304
Val Tyr Gly Gly Gln Ser Gln Trp Arg Val Tyr Leu Asn Asn Gln Glu
            755                 760                 765 atc ggc caa tgg gtt ggc aat agt gag gat acc ttc agc cac aca cct      2352
Ile Gly Gln Trp Val Gly Asn Ser Glu Asp Thr Phe Ser His Thr Pro
        770                 775                 780 tct gtc tat ttg gac gga cat tcg gcg att cgt att aag ttc cgg ggt      2400
Ser Val Tyr Leu Asp Gly His Ser Ala Ile Arg Ile Lys Phe Arg Gly
785                 790                 795                 800 gtc gaa atc cac aag ggt gat act ttg aag att gtc ggt atg cct gat      2448
Val Glu Ile His Lys Gly Asp Thr Leu Lys Ile Val Gly Met Pro Asp
                805                 810                 815 ggc act gag ccg gcg cca ttg gac tat gtg gct ttg ctg ccg gcg ggt      2496
Gly Thr Glu Pro Ala Pro Leu Asp Tyr Val Ala Leu Leu Pro Ala Gly
                820                 825                 830 att gta gat tag                                                      2508
Ile Val Asp
        835

<210> SEQ ID NO 2
<211> LENGTH: 835
<212> TYPE: PRT
<213> ORGANISM: Penicillium aurantiogriseum

<400> SEQUENCE: 2

Met Arg Ala Leu Leu Phe Phe Ala Ser Leu Gly Phe Ala Ala Ala Glu
1               5                   10                  15

Asn Gly Leu Asn Gly Trp Leu Arg Tyr Ala Ser Leu Pro Cys Ser Gly
            20                  25                  30

Gln Cys His Pro Asn Leu Pro Ser Ser Ile Val Thr Leu Asn Ala Thr
        35                  40                  45

Glu Thr Ser Pro Val Tyr Val Ala Gly Thr Glu Leu Gln Ser Gly Leu
    50                  55                  60

Lys Gly Val Tyr Gly Lys Ser Val Gln Val Ala His Asn Lys Cys Lys
65                  70                  75                  80

Thr Ser Ser Ser Val Val Val Gly Thr Val Asp Gln Tyr Arg Glu Ser
                85                  90                  95

Cys Gly Pro Val Lys Asn Val Pro Glu Leu Glu Glu Asp Gly Phe Trp
            100                 105                 110
```

-continued

```
Leu Asp Thr Lys Gly Glu Asn Val Gln Ile Leu Gly Gln Asn Glu Arg
        115                 120                 125
Gly Ala Leu Tyr Gly Thr Phe Glu Tyr Leu Ser Met Leu Ala Gln Gly
    130                 135                 140
Asn Phe Ser Lys Val Ala Tyr Ala Ser Asn Pro Ser Ala Pro Ile Arg
145                 150                 155                 160
Trp Val Asn Gln Trp Asp Asp Leu Asp Gly Arg Ile Glu Arg Gly Tyr
                165                 170                 175
Gly Gly Pro Ser Ile Phe Phe Lys Asp Gly Gln Ile Val Asp Asp Leu
            180                 185                 190
Thr Arg Val Thr Glu Tyr Ala Arg Leu Leu Ala Ser Ile Arg Ile Asn
        195                 200                 205
Ala Val Val Ile Asn Asn Val Asn Ala Asp Ala Leu Leu Asn Ser
    210                 215                 220
Thr Asn Leu Asp Gly Val Ala Arg Ile Ala Asp Val Phe Arg Pro Tyr
225                 230                 235                 240
Gly Ile Gln Val Gly Leu Ser Leu Asn Phe Ala Ser Pro Lys Thr Asp
                245                 250                 255
Gly Gly Leu Asn Thr Phe Asp Pro Leu Asp Ala Ser Val Ile Glu Trp
            260                 265                 270
Trp Ser Asn Ile Thr Thr Gln Val Tyr Glu Arg Val Pro Asp Met Ala
        275                 280                 285
Gly Tyr Leu Val Lys Ala Asp Ser Glu Gly Glu Pro Gly Pro Gln Thr
    290                 295                 300
Tyr Asn Arg Thr Leu Ala Glu Ala Ala Asn Leu Phe Ala Lys Glu Val
305                 310                 315                 320
Gln Pro Tyr Gly Gly Ile Val Met Tyr Arg Ala Phe Val Tyr Asn Lys
                325                 330                 335
Leu Asn Glu Ser Ile Trp Thr Asp Arg Ala Lys Ala Ala Val Gly
            340                 345                 350
Phe Phe Lys Asp Leu Asp Gly Glu Phe Asp Asp Asn Val Val Ile Gln
        355                 360                 365
Ile Lys Tyr Gly Pro Ile Asp Phe Gln Val Arg Glu Pro Ala Ser Ala
    370                 375                 380
Leu Phe Ala Asn Leu Phe Asn Thr Ser Met Ala Ile Glu Leu Gln Val
385                 390                 395                 400
Thr Gln Glu Tyr Leu Gly Gln Gln Ser His Leu Val Tyr Val Ala Pro
                405                 410                 415
Leu Trp Lys Thr Ile Leu Asp Ser Asp Leu Arg Val Asp Gly Gln Pro
            420                 425                 430
Ser Leu Val Arg Asp Ile Val Thr Gly Lys Arg Phe Asn Arg Lys Leu
        435                 440                 445
Gly Gly Ser Ala Ala Val Val Asn Val Gly Thr Asn Thr Thr Trp Leu
    450                 455                 460
Gly Ser His Leu Ser Met Ser Asn Leu Tyr Ala Tyr Gly Arg Leu Ala
465                 470                 475                 480
Trp Asn Pro Ala Asp Asp Ala Gln Asp Ile Leu Gln Asp Trp Ile Arg
                485                 490                 495
Leu Thr Phe Gly Leu Asp Arg Lys Val Leu Asp Thr Ile Thr Arg Met
            500                 505                 510
Ser Met Glu Ser Trp Pro Ala Tyr Glu Gln Tyr Ser Gly Asn Leu Gly
        515                 520                 525
Ile Gln Thr Leu Thr Asp Ile Leu Tyr Thr His Tyr Gly Pro Asn Pro
    530                 535                 540
```

-continued

```
Ala Ser Gln Asp Asn Asn Gly Trp Gly Gln Trp Thr Arg Ala Asp Gln
545                 550                 555                 560

Thr Ser Ile Gly Met Asp Arg Thr Val Ala Asn Gly Thr Gly Phe Ser
                565                 570                 575

Gly Gln Tyr Pro Asp Glu Ile Ala Ala Met Tyr Glu Asn Ile Asp Thr
            580                 585                 590

Thr Pro Asp Asp Leu Leu Leu Trp Phe His His Val Lys Tyr Thr His
        595                 600                 605

Arg Leu His Ser Gly Lys Thr Val Ile Gln His Phe Tyr Asp Glu His
    610                 615                 620

Tyr Ser Gly Ala Glu Thr Ala Gln Thr Phe Leu Thr Gln Trp Glu Ser
625                 630                 635                 640

Leu His Gly Lys Ile Asp Ala Glu Arg Tyr Asn His Thr Arg His Phe
                645                 650                 655

Leu Asp Tyr Gln Ser Gly His Ser Ile Val Trp Arg Asp Ala Ile Asn
            660                 665                 670

Asp Phe Tyr Tyr Asn Leu Ser Gly Ile Pro Asp Glu Ala Lys Arg Val
        675                 680                 685

Gly His His Pro Trp Arg Ile Glu Ala Glu Asp Met Lys Leu Glu Gly
    690                 695                 700

Tyr Lys Thr Tyr Thr Val Ser Pro Phe Glu Thr Ala Ser Gly Ser Val
705                 710                 715                 720

Ala Ile Val Thr Thr Ser Asn Ser Thr Ala Gly Thr Ala Ser Thr Lys
                725                 730                 735

Ile Asn Phe Pro Ser Gly Thr Tyr Asp Leu Ala Val Asn Tyr Tyr Asp
            740                 745                 750

Val Tyr Gly Gly Gln Ser Gln Trp Arg Val Tyr Leu Asn Asn Gln Glu
        755                 760                 765

Ile Gly Gln Trp Val Gly Asn Ser Glu Asp Thr Phe Ser His Thr Pro
    770                 775                 780

Ser Val Tyr Leu Asp Gly His Ser Ala Ile Arg Ile Lys Phe Arg Gly
785                 790                 795                 800

Val Glu Ile His Lys Gly Asp Thr Leu Lys Ile Val Gly Met Pro Asp
                805                 810                 815

Gly Thr Glu Pro Ala Pro Leu Asp Tyr Val Ala Leu Leu Pro Ala Gly
            820                 825                 830

Ile Val Asp
        835
```